United States Patent
Ludwin et al.

(10) Patent No.: US 8,523,787 B2
(45) Date of Patent: Sep. 3, 2013

(54) DETECTION OF TENTING

(75) Inventors: Doron Moshe Ludwin, Haifa (IL); Eliahu Zino, Atlit (IL)

(73) Assignee: Biosense Webster (Israel), Ltd., Yokneam (IL)

( * ) Notice: Subject to any disclaimer, the term of this patent is extended or adjusted under 35 U.S.C. 154(b) by 0 days.

(21) Appl. No.: 13/152,423

(22) Filed: Jun. 3, 2011

(65) Prior Publication Data
US 2012/0310116 A1    Dec. 6, 2012

(51) Int. Cl.
*A61B 5/103* (2006.01)
*A61B 5/107* (2006.01)

(52) U.S. Cl.
USPC ........... 600/587; 600/437; 600/438; 600/462; 600/551; 600/552; 600/553; 600/557

(58) Field of Classification Search
USPC .............. 600/437, 438, 462, 551, 552, 553, 600/557, 587
See application file for complete search history.

(56) References Cited

U.S. PATENT DOCUMENTS

| | | | |
|---|---|---|---|
| 5,391,199 A | 2/1995 | Ben-Haim | |
| 5,944,022 A | 8/1999 | Nardella et al. | |
| 5,983,126 A | 11/1999 | Wittkampf | |
| 6,239,724 B1 | 5/2001 | Doron et al. | |
| 6,332,089 B1 | 12/2001 | Acker et al. | |
| 6,351,549 B1 * | 2/2002 | Souluer | 382/131 |
| 6,456,864 B1 | 9/2002 | Swanson et al. | |
| 6,484,118 B1 | 11/2002 | Govari | |
| 6,569,098 B2 * | 5/2003 | Kawchuk | 600/437 |
| 6,618,612 B1 | 9/2003 | Acker et al. | |
| 6,690,963 B2 | 2/2004 | Ben-Haim et al. | |
| 7,297,116 B2 * | 11/2007 | Varghese et al. | 600/438 |
| 7,435,232 B2 * | 10/2008 | Liebschner | 600/587 |
| 8,043,216 B2 * | 10/2011 | Matsumura | 600/438 |
| 8,137,275 B2 * | 3/2012 | Fan et al. | 600/438 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0064038 A1 * | 3/2006 | Omata et al. | 600/587 |
| 2006/0173480 A1 | 8/2006 | Zhang | |
| 2007/0167818 A1 * | 7/2007 | Osborn et al. | 600/462 |
| 2007/0167819 A1 * | 7/2007 | Osborn et al. | 600/462 |
| 2008/0200843 A1 * | 8/2008 | Williams et al. | 600/587 |
| 2008/0249467 A1 * | 10/2008 | Burnett et al. | 604/117 |
| 2008/0269606 A1 * | 10/2008 | Matsumura | 600/438 |
| 2009/0093806 A1 | 4/2009 | Govari et al. | |
| 2009/0138007 A1 | 5/2009 | Govari et al. | |
| 2009/0234206 A1 * | 9/2009 | Gaspard et al. | 600/322 |
| 2009/0306509 A1 * | 12/2009 | Pedersen et al. | 600/446 |
| 2009/0306515 A1 * | 12/2009 | Matsumura et al. | 600/459 |
| 2010/0160778 A1 * | 6/2010 | Eskandari et al. | 600/438 |
| 2011/0054354 A1 * | 3/2011 | Hunter et al. | 600/587 |
| 2011/0054355 A1 * | 3/2011 | Hunter et al. | 600/587 |
| 2011/0071436 A1 * | 3/2011 | Althoefer et al. | 600/587 |
| 2011/0172538 A1 * | 7/2011 | Sumi | 600/453 |
| 2012/0184864 A1 * | 7/2012 | Harlev et al. | 600/509 |
| 2012/0184865 A1 * | 7/2012 | Harlev et al. | 600/509 |
| 2012/0316407 A1 * | 12/2012 | Anthony et al. | 600/301 |

FOREIGN PATENT DOCUMENTS

WO    WO 96/05768 A1    2/1996

* cited by examiner

*Primary Examiner* — Sean Dougherty

(57) ABSTRACT

A method, including measuring a force exerted by a probe on tissue of a patient and measuring a displacement of the probe while measuring the force. The method further includes detecting a tenting of the tissue responsively to a relation between the measured force and the measured displacement.

20 Claims, 5 Drawing Sheets

DETECTION OF TENTING

FIELD OF THE INVENTION

The present invention relates generally to medical procedures, and specifically to detection of tenting during a procedure.

BACKGROUND OF THE INVENTION

Invasive medical procedures using a catheter probe typically involve the probe contacting internal tissue of the patient undergoing the procedure. Such contact typically involves the probe applying force to the tissue, and the force in turn may cause unwanted tenting of the tissue.

U.S. Patent Application 2006/0173480 to Zhang, whose disclosure is incorporated herein by reference, describes a system which is stated to more accurately control insertion of penetrating instruments (e.g., trocars, needles, or the like) into a body cavity, organ, or potential space. The disclosure describes coupling an accelerometer to the penetrating instrument, so as to achieve the control.

Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The description above is presented as a general overview of related art in this field and should not be construed as an admission that any of the information it contains constitutes prior art against the present patent application.

SUMMARY OF THE INVENTION

An embodiment of the present invention provides a method, including:

measuring a force exerted by a probe on tissue of a patient;

measuring a displacement of the probe while measuring the force; and detecting a tenting of the tissue responsively to a relation between the measured force and the measured displacement.

Typically, detecting the tenting includes confirming that the relation consists of a mathematically direct relationship between a first magnitude of a change in the measured force and a second magnitude of the measured displacement. The method may further include measuring the change in the measured force in a direction defined by the measured displacement.

In a disclosed embodiment measuring the force includes measuring a change in the force, and detecting the tenting includes determining that the change in the force is greater than a preset force change range.

In a further disclosed embodiment detecting the tenting includes determining that the displacement is greater than a preset displacement range.

The method may include measuring a size of the tenting in response to the measured displacement.

Typically, the method includes issuing a warning to an operator of the probe in response to detecting the tenting.

In an alternative embodiment the method includes adjusting a map of coordinates of the tissue in response to detecting the tenting. Typically, the tenting of the tissue includes a conical formation in the tissue, and adjusting the map includes preparing the map absent a location of an apex of the conical formation. Typically, preparing the map includes determining a location of a base of the conical formation and using coordinates of the location of the base in preparing the map.

In another alternative embodiment the method includes correcting the measured force in response to at least one of a heartbeat and a respiration of the patient.

There is further provided, according to an embodiment of the present invention, apparatus, including:

a probe including:

a force sensor configured to measure a force exerted by the probe on tissue of a patient, and a position transducer configured to measure a displacement of the probe while the force sensor is measuring the force; and a processor which is configured to detect a tenting of the tissue responsively to a relation between the measured force and the measured displacement.

There is further provided, according to an embodiment of the present invention, a computer software product including a tangible computer-readable medium having non-transitory computer program instructions recorded therein, which instructions, when read by a computer, cause the computer to:

measure a force exerted by a probe on tissue of a patient;

measure a displacement of the probe while measuring the force; and detect a tenting of the tissue responsively to a relation between the measured force and the measured displacement.

The present disclosure will be more fully understood from the following detailed description of the embodiments thereof, taken together with the drawings, in which:

DETAILED DESCRIPTION OF EMBODIMENTS

Overview

An embodiment of the present invention provides a method for detection of tenting in body tissue of a patient. The method may typically be applied while a patient is undergoing a medical procedure comprising insertion of a probe into a chamber of the patient's heart. The method comprises measuring the force exerted by the probe on the body tissue. In the case of the heart procedure the tissue is typically the endocardium. While the force is being measured, the displacement of the tissue is also measured. Both measurements may be made using respective sensors in the probe, one measuring the position of the probe, the other measuring the force exerted by the probe on the tissue.

Tenting may be detected by observing the behavior of the measured force compared to that of the measured displacement, i.e., by observing how the two parameters are related. Typically, if the force, measured in the direction of the displacement, increases as the displacement increases, i.e., if there is a mathematically direct relationship between the magnitude of the force and the magnitude of the displacement, tenting is occurring.

The direct relationship occurring during tenting is in contrast to the typical relationship if no tenting occurs. In the case of a probe contacting the endocardium, typically the beating of the heart, and/or the respiration of the patient, cause both the displacement of the probe and the force measured by the probe to change. However, in a "normal," non-tenting situation, the force typically decreases as the displacement increases, so that the two quantities have a mathematically inverse relationship.

The direct relationship between the force and the displacement that occurs during tenting thus provides a clear, simple indication for tenting detection.

System Description

Figure 1:
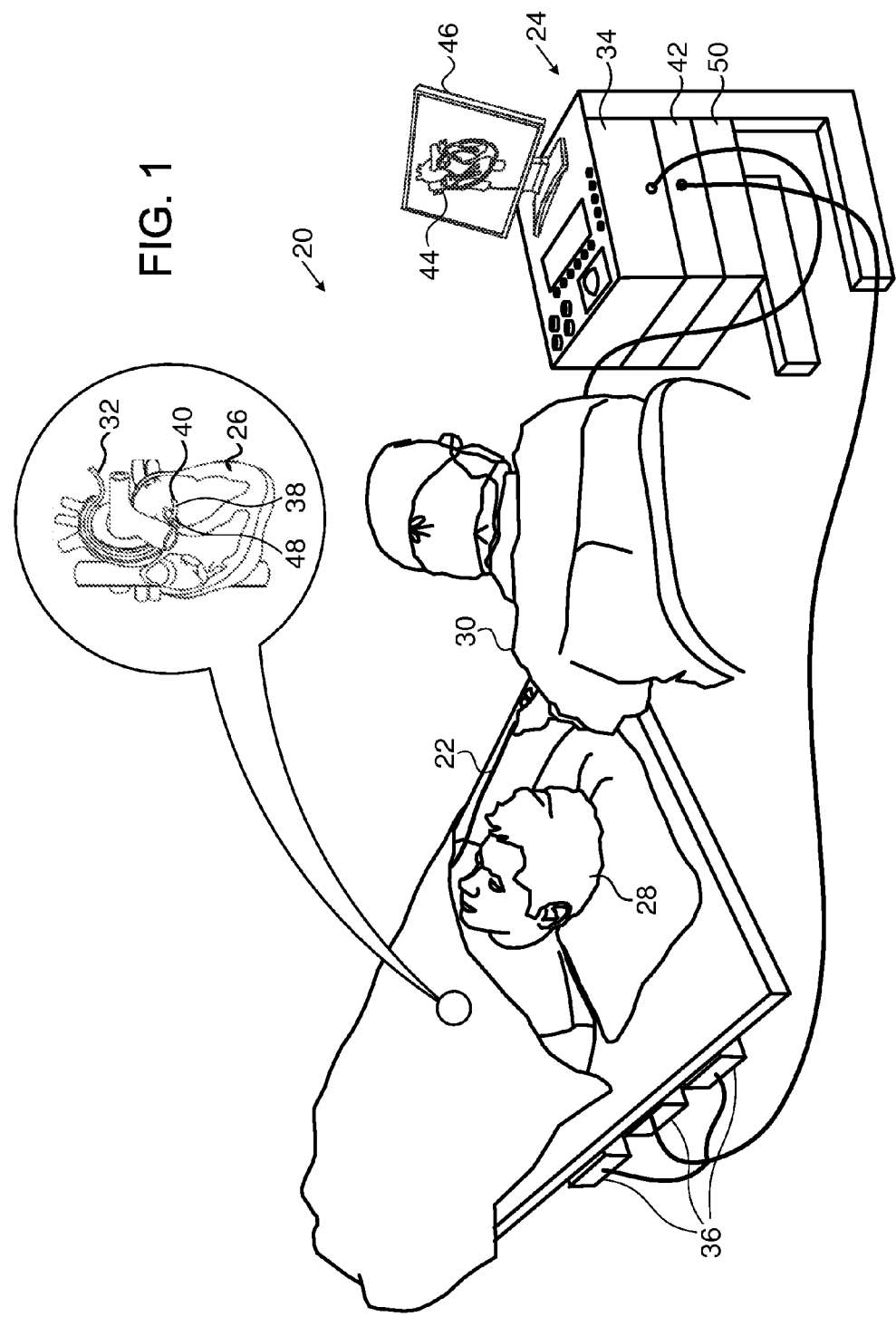
FIG. 1 is a schematic illustration of a tenting detection system, according to an embodiment of the present invention.
Figure 2:
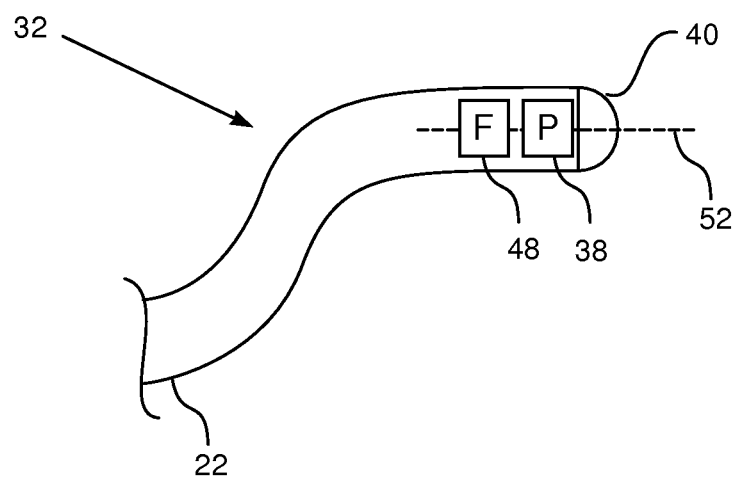
FIG. 2 is a schematic diagram of a distal end of a probe used in the system, according to an embodiment of the present invention.

Reference is now made to FIG. 1, which is a schematic illustration of a tenting detection system 20, and to FIG. 2, which is a schematic diagram of a distal end of a probe used in the system, according to embodiments of the present invention. System 20 comprises a probe 22, herein assumed to be a catheter, and a control console 24. In the embodiment described herein, it is assumed by way of example that probe 22 may be used for mapping electrical potentials in a heart 26 of a patient 28. Alternatively or additionally, probe 22 may be used for other therapeutic and/or diagnostic purposes, such as for ablation, in the heart or in another body organ.

Console 24 comprises a processor 42, typically a general-purpose computer, with suitable front end and interface circuits for receiving signals from probe 22 and for controlling the other components of system 20 described herein. Processor 42 may be programmed in software to carry out the functions that are used by the system, and the processor stores data for the software in a memory 50. The software may be downloaded to console 24 in electronic form, over a network, for example, or it may be provided on non-transitory tangible media, such as optical, magnetic or electronic memory media. Alternatively, some or all of the functions of processor 42 may be carried out by dedicated or programmable digital hardware components.

An operator 30 inserts probe 22 through the vascular system of patient 28 so that a distal end 32 of probe 22 enters a chamber of heart 26. System 20 typically uses magnetic position sensing to determine position coordinates of the distal end inside heart 26. In this case console 24 comprises a driver circuit 34, which drives magnetic field generators 36 placed at known positions external to patient 28, e.g., below the patient's torso. A magnetic field sensor 38 within the distal end of the probe generates electrical position signals in response to the magnetic fields from the coils, thereby enabling processor 42 to determine the position, i.e., the location and typically also the orientation, of distal end 32 within the chamber. Sensor 38, also referred to herein as sensor "P," typically comprises one or more coils, usually three coils orthogonal to each other. This method of position sensing is implemented, for example, in the CARTO™ system, produced by Biosense Webster Inc. (Diamond Bar, Calif.) and is described in detail in U.S. Pat. Nos. 5,391,199, 6,690,963, 6,484,118, 6,239,724, 6,618,612 and 6,332,089, in PCT Patent Publication WO 96/05768, and in U.S. Patent Application Publications 2002/0065455 A1, 2003/0120150 A1 and 2004/0068178 A1, whose disclosures are all incorporated herein by reference.

In an alternative embodiment, the roles of position sensor 38 and magnetic field generators 36 may be reversed. In other words, driver circuit 34 may drive a magnetic field generator in distal end 32 to generate one or more magnetic fields. The coils in generator 36 may be configured to sense the fields and generate signals indicative of the amplitudes of the components of these magnetic fields. Processor 42 receives and processes these signals in order to determine the position of distal end 32 within heart 26.

Although in the present example system 20 is assumed to measure the position of distal end 32 using magnetic-based sensors, embodiments of the present invention may use other position tracking techniques, for example, tracking systems based on impedance measurements. Impedance-based position tracking techniques are described, for example, in U.S. Pat. Nos. 5,983,126, 6,456,864 and 5,944,022, whose disclosures are also incorporated herein by reference. Other position tracking techniques, known to one having ordinary skill in the art, may be used to determine the position of distal end 32. Thus, in the present application, the term "position transducer" is used to refer to any element which provides signals, according to the location and orientation of a probe or a section of a probe, such as the probe's distal end, to console 24.

Distal end 32 also comprises a force sensor 48, also referred to herein as sensor "F," which is able provide electrical force signals to processor 42 in order to measure the magnitude and direction of the force on the distal end. The direction of the force is typically measured relative to a symmetry axis 52 of the distal end. Various techniques may be used in measuring the force. Components and methods that may be used for this purpose are described, for example, in U.S. Patent Application Publications 2009/0093806 and 2009/0138007, whose disclosures are incorporated herein by reference and which are assigned to the assignee of the present patent application. These patent applications describe a probe whose distal tip is coupled to the distal end of the probe by a spring-loaded joint, which deforms in response to pressure exerted on the distal tip when it engages tissue. A magnetic position sensing assembly within the probe, comprising transmitting and receiving coils on opposite sides of the joint, senses the position of the distal tip relative to the distal end of the probe. Changes in this relative position are indicative of deformation of the spring and thus give an indication of the magnitude and direction of the force on the probe, i.e., on its distal tip.

In order to map the chamber of heart 26, operator 30 manipulates probe 22 so that distal end 32 is at multiple locations on (or in close proximity to) the inner surface of the chamber. At each location, an electrode 40 coupled to the distal end measures a certain physiological property (e.g., the local surface electrical potential). Processor 42 correlates the location measurements, derived from the position signals of sensor 38, and the electrical potential measurements. Thus, the system collects multiple map points, with each map point comprising a coordinate on the inner chamber surface and a respective physiological property measurement at this coordinate.

Processor 42 uses the coordinates of the map points to construct a simulated surface of the cardiac chamber in question. An example method for constructing the simulated surface is described further below. Processor 42 then combines the electrical potential measurements of the map points with the simulated surface to produce a map of the potentials overlaid on the simulated surface. Processor 42 displays an image 44 of the map to operator 30 on a display 46.

Figure 3:
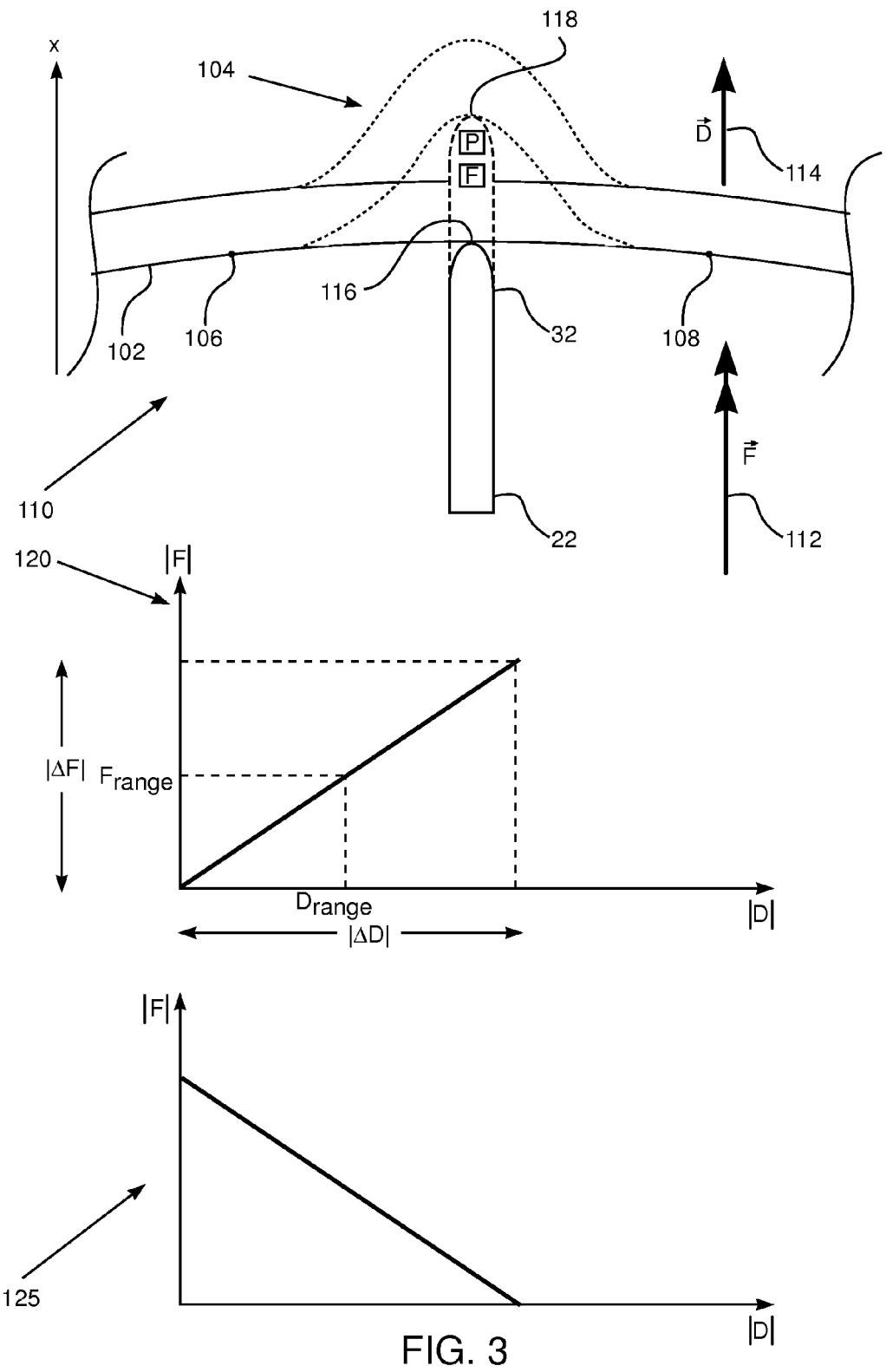
FIG. 3 illustrates a tenting situation that may be generated during the manipulation of a probe, according to an embodiment of the present invention.
Figure 4:
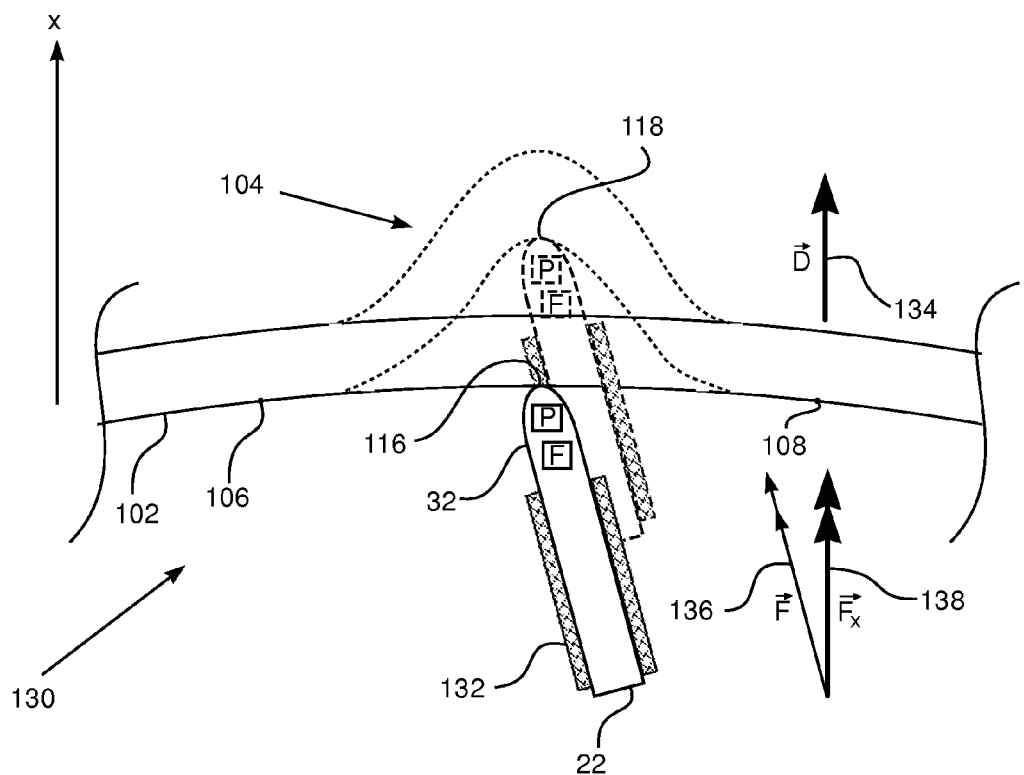
FIG. 4 illustrates another tenting situation that may be generated during the manipulation of a probe, according to an embodiment of the present invention.
Figure 4:
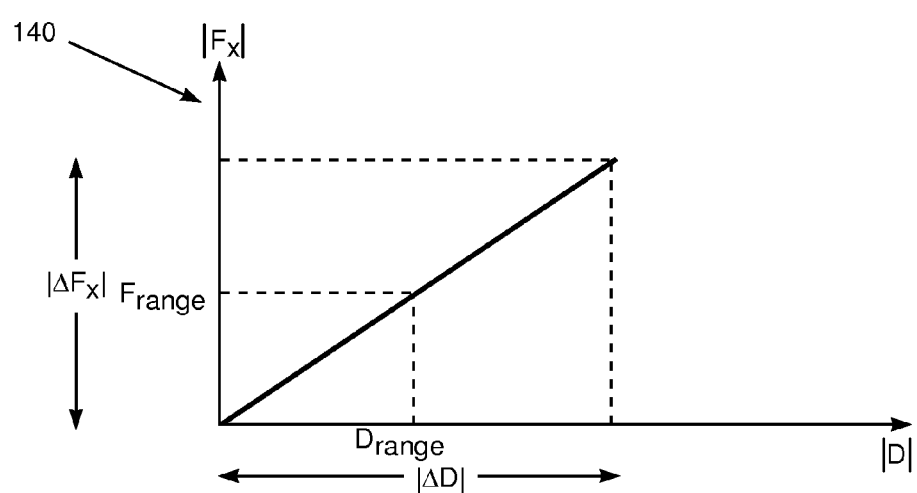

FIG. 3 and FIG. 4 respectively illustrate first and second tenting situations that may be generated during the manipulation of probe 22 by operator 30, according to embodiments of the present invention. Tenting is the formation of a local generally conical structure, or "tent," in tissue, herein assumed to be a heart wall 102, and is typically caused by excessive force on a region 104 of the tissue, causing the region to form a tenting cone. The excessive force is typically caused by the distal tip of the probe pushing against region 104, the contact location of the tip with the region forming an apex of the tent. During reconstruction of the region, the tenting effect may also be observed as a conical formation, or tent, in the reconstruction.

Processor 42 may use a surface reconstruction algorithm, which typically connects the outermost points of a set of mapped locations of the heart wall, to generate the surface map of the wall. By way of example, points 106 and 108 are assumed to be comprised within the set of mapped points. In this case, a tented region such as region 104 may cause significant deformation in the map, as described above. More seriously, excessive tenting may lead to perforation of the heart wall at the tenting site. As is described herein, embodiments of the present invention provide a warning to operator 30 that tenting is occurring, and also correct for any deformation in the surface map caused by the tenting.

The inventors have observed that tenting typically occurs when the force between a probe and tissue contacted by the probe grows as the probe moves forward in the direction of the force. Such a scenario typically occurs if the distal end of the probe engages the tissue head-on. An alternative scenario occurs when a guiding sheath around the probe constrains the probe to engage the tissue in a non-head-on, or oblique, direction. In this case, while the orientation of the probe to the tissue is oblique, the motion of the probe is in the same direction as the resolved force on the tissue. In both cases, the magnitude of the force and the magnitude of the displacement are in a mathematically direct relationship with each other, i.e., as the magnitude of the force increases, the magnitude of the displacement also increases.

The latter property contrasts with the typical case of a probe in contact with a "normal" heart wall, wherein, as the wall moves away from the probe, due to the heart beating and/or due to respiration, the magnitude of the force measured by the probe decreases while the magnitude of the displacement increases. Such a mathematically inverse relationship, i.e., where the force decreases as the displacement increases, occurs regardless of whether the contact between the probe and the heart wall is head-on or oblique.

A diagram 110 (FIG. 3) illustrates a first tenting situation wherein distal end 32 is in contact with, and exerting a force on, heart wall 102. In this situation, probe 22 engages wall 102 in a head-on manner. An arrow 112 represents the force vector exerted by the probe on region 104, as measured by force sensor F. An arrow 114 represents the displacement vector of the probe from a position 116, where tenting begins to occur, to a position 118, in region 104, where the tenting terminates. By way of example, the direction of the displacement is assumed to define the direction of a local x-axis for region 104. Position 118 corresponds to the apex of the tenting cone formed in region 104, and the displacement vector may be derived from locations measured by position sensor P. As is illustrated in the diagram, the force vector and the displacement vector are parallel.

A schematic graph 120 plots the magnitude of the force |F| vs. the magnitude of the displacement |D|, as the tenting situation develops, i.e., as the distal tip of the probe moves from position 116 to position 118. As is illustrated by the graph sloping upward to the right, in the case of tenting the two magnitudes are directly related.

For comparison, a schematic graph 125 plots the magnitude of the force |F| vs. the magnitude of the displacement |D|, when no tenting is present, i.e., during motion of the heart wall due to the heart beating and/or respiration. In this no tenting case, as the displacement magnitude increases the force magnitude decreases, so the two magnitudes are inversely related. This is illustrated by the graph sloping downward to the right.

A diagram 130 (FIG. 4) illustrates a second tenting situation wherein distal end 32 is in contact with, and exerting a force on, heart wall 102. In this second situation, probe 22 is constrained by a sheath 132 to engage wall 102 obliquely. An arrow 134, substantially the same as arrow 114, represents the displacement vector of the probe from initial tenting position 116. An arrow 136 represents the overall force vector exerted by the probe on region 104, and an arrow 138 represents the force vector resolved in the direction of the displacement, i.e., parallel to the x-axis. In the second tenting situation the direction of the overall force is not parallel to the displacement, and in one embodiment the magnitude of the resolved force in the direction of the displacement is typically approximately of the order of 80%, depending on the degree of obliquity, of the value of the magnitude of the overall force. 80% corresponds to an obliquity of approximately 30°, but embodiments of the present invention encompass other angles, which may be more or less than 30°, such as 45°.

A schematic graph 140 plots the magnitude of the resolved force $|F_x|$ vs. the magnitude of the displacement |D|, as the second tenting situation develops. As is illustrated by the graph, the two magnitudes in the second tenting situation are also directly related.

The quantities $F_{range}$, $D_{range}$, |ΔD|, |ΔF|, and $|ΔF_x|$, shown in graphs 120 and 140, are described below, with reference to the flow chart of FIG. 5.

Figure 5:
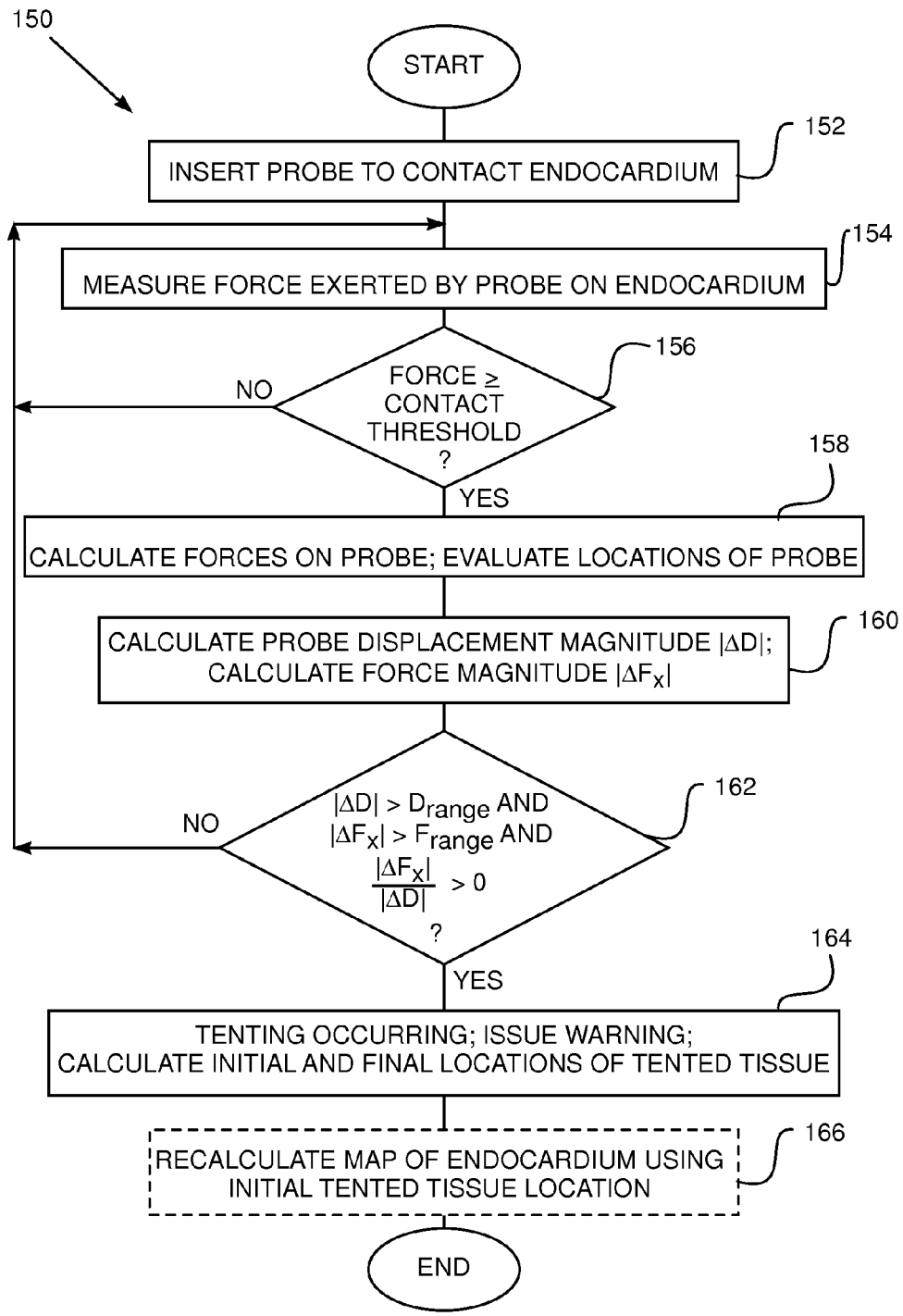
FIG. 5 is a flow chart of a process for detecting tenting, according to an embodiment of the present invention.

FIG. 5 is a flow chart 150 of a process for detecting tenting, according to an embodiment of the present invention. The process uses the characteristics described above with reference to FIGS. 3 and 4, concerning the relationship between the force and the displacement, and by way of example is directed towards detecting tenting in the endocardium.

In a first step 152, operator 30 inserts probe 22 into patient 28 so that distal end 32 of the probe enters a chamber of heart 26. The probe is inserted until it contacts the endocardium. The contact with the endocardium may be detected by a number of different methods, such as by observing that the potential on electrode 40 corresponds to that generated by the endocardium, determining that the force measured by force sensor 48 is above a zero level of the sensor, and/or determining that the position registered by position sensor 38 corresponds to coordinates of the endocardium. The endocardium coordinates may be determined from prior measurements with position sensor 38, and/or by imaging heart 26 with systems using ultrasound, fluoroscopy, or magnetic resonance imaging.

In step 152 the probe, without a surrounding sheath, may be inserted to contact the endocardium, as is illustrated schematically in FIG. 3. Alternatively, the probe may have a surrounding sheath, as is illustrated in FIG. 4.

In a force measurement step 154, processor 42 uses the signals from force sensor 48 to calculate a magnitude of the force exerted by the distal end of probe 22 on the tissue of the endocardium. The processor also evaluates the direction of the force, relative to symmetry axis 52 of the distal end (FIG. 2), from the signals.

In a first comparison step 156, the processor checks if the magnitude of the force is greater than or equal to a preset contact threshold value. A typical value for the contact threshold is approximately 3 g. If the magnitude is less than the contact threshold, the process returns to step 154. If the magnitude exceeds the threshold, processor 42 continues to a force and displacement measurement step 158.

In force and displacement measurement step 158, the processor calculates, while the magnitude of the force is greater than the contact threshold used in step 156, values of the magnitude and the direction of the force. Simultaneously, processor 42 uses the signals from position sensor 38 to evaluate locations of the distal end of the probe. The values are assumed to be measured over a period of time herein termed the measurement period. The processor stores the values of the force magnitude and direction, and the values of the locations, in memory 50.

In an evaluation step 160, the processor analyzes the values stored in memory 50.

From analysis of the location values the processor determines the overall displacement vector, $\vec{\Delta D}$, of the distal end, from the difference between the final location and the initial location of the distal end for the measurement period. Displacement vector $\vec{\Delta D}$ has a direction and magnitude, and the direction is herein assumed to define the direction of a local x-axis (as illustrated in FIGS. 3 and 4). The processor also calculates the magnitude, $|\Delta D|$, of the overall displacement. The displacement magnitude $|\Delta D|$ is used in graphs 120 and 140.

From analysis of the force measurement values, the processor determines directions of the force during the measurement period. Typically, for an unsheathed probe the force directions are parallel to the direction of the overall displacement, i.e., are parallel to the local x-axis, as is illustrated in FIG. 3. Typically, for a sheathed probe, the force directions are parallel to the sheath and are oblique to the local x-axis, as is illustrated in FIG. 4.

For each force measurement taken in the measurement period, the processor calculates a force vector, $\vec{F}$, as a direction and as a magnitude $|F|$. The processor resolves the force vector $\vec{F}$ along the local x-axis, and determines resolved magnitudes of the force, $|F_x|$. (For the head-on case of FIG. 3 the resolved and unresolved forces are equal; however, for the oblique case of FIG. 4 the resolved force is less than the unresolved force.) From the final and initial resolved force magnitudes, respectively corresponding to the final and initial locations of the distal end, the processor calculates the value of an overall change in resolved force magnitude, $|\Delta F_x|$. Graph 140 illustrates the change in resolved force magnitude $|\Delta F_x|$. Graph 120 illustrates the change in overall force magnitude $|\Delta F|$; since the graph is for a head on situation, $|\Delta F| \cong |\Delta F_x|$.

In a second comparison step 162, the processor checks if the following inequalities are valid:

$$|\Delta D| > D_{range} \quad (1)$$

$$|\Delta F_x| > F_{range} \quad (2)$$

$$\frac{|\Delta F_x|}{|\Delta D|} > 0 \quad (3)$$

$D_{range}$ and $F_{range}$ are preset minimum ranges of $|\Delta D|$ and $|\Delta F_x|$ that are used by processor 42, and that are illustrated in graphs 120 and 140. Typical values for $D_{range}$ and $F_{range}$ are approximately 4 mm and approximately 8 g respectively. The processor uses inequalities (1) and (2) to ensure that the values used to check inequality (3) are not too small. Using values that are too small could cause the check of inequality (3) to be adversely affected, e.g., by noise.

The validity of inequality (3) determines that the relationship between $|\Delta D|$ and $|\Delta F_x|$ is a mathematically direct relationship, so that as the magnitude of the displacement increases the magnitude of the resolved force also increases. The direct relationship is illustrated by graphs 120 and 140.

It will be understood that inequality (3) is typically invalid during normal beating of the heart and respiration of the patient, wherein as the magnitude of the displacement increases the magnitude of the resolved force decreases, so that the relationship is an inverse relationship. Such an inverse relationship is illustrated by graph 125. Thus the validity of inequality (3) confirms that tenting is occurring, and that the changes in force and displacement are not typical of the normal behavior of the heart.

If any of inequalities (1), (2), and (3) are invalid, the flow chart returns to step 154.

If all inequalities (1), (2), and (3) are valid, the processor proceeds to a warning step 164.

In warning step 164, the processor assumes that tenting may be occurring, and issues a visual and/or audible warning to operator 30, for instance, by placing a notice on display 46, that tenting may be occurring. The processor may also calculate a size of the tenting, by using the results stored in memory 50 to find initial location 116 (FIGS. 3 and 4) of the tented tissue (the point at which the tenting began), and final location 118 of the tented tissue, the apex of the tent formed. The size may be included in the warning. In some embodiments, if the tenting size is greater than a preset value, the warning may be enhanced to reflect a possible dangerous situation. A dangerous tenting size typically depends on the thickness of the tissue that is undergoing the tenting. The thickness of the tissue may be known, or may be estimated, for example from a knowledge of location 116. Alternatively or additionally, a dangerous situation may be assumed if $$\frac{|\Delta F_x|}{|\Delta D|} > Q,$$

where Q is a positive value, typically greater than 2 g/mm.

An optional mapping step 166 (shown as optional by broken lines in the flow chart) is typically implemented if the processor is generating a map of the locations of the endocardium using a mapping algorithm. In step 166, the processor replaces location 118 of the tent apex with initial location 116 of the tented tissue, calculated in step 164, and uses this value as the location of the tissue. The replaced location is used for recalculating the map using the mapping algorithm.

Flow chart 150 then ends.

The description of the steps of flow chart 150 has assumed that the forces measured by force sensor F have not undergone any correction due to heartbeat and/or respiration of the patient. Some embodiments of the present invention may apply such a correction, for example, by measuring or estimating the forces applied to the force sensor from a "typical" heart, over a number of heartbeats and respiration cycles, so as to determine a typical force vs. time relationship for the force sensor. The processor may use the relationship to find the expected typical force measurement at times when tenting may be occurring, and subtract these typical force measurements from the actual forces measured by the force sensor. The corrected forces may then be used in inequalities (2) and (3) above.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

We claim:

1. A method for detecting the tenting of tissue in a patient caused by a force-sensing medical probe, capable of use with a three-dimensional mapping and navigation system, inserted into the patient and contacting the tissue of the patient, comprising:
   measuring a force exerted by the medical probe on the tissue of a patient using the mapping and navigation system;
   measuring a spatial displacement of the probe using the mapping and navigation system while measuring the force; and
   detecting a tenting of the tissue responsively to a relation between the measured force and the measured displacement, wherein detecting the tenting comprises confirming that the relation comprises a mathematically direct relationship between a first magnitude of a change in the measured force and a second magnitude of the measured displacement.

2. The method according to claim 1, further comprising measuring the change in the measured force in a direction defined by the measured displacement.

3. A method for detecting the tenting of tissue in a patient caused by a force-sensing medical probe, capable of use with a three-dimensional mapping and navigation system, inserted into the patient and contacting the tissue of the patient, comprising:
   measuring a force exerted by the medical probe on the tissue of a patient using the mapping and navigation system;
   measuring a spatial displacement of the probe using the mapping and navigation system while measuring the force; and
   detecting a tenting of the tissue responsively to a relation between the measured force and the measured displacement, wherein measuring the force comprises measuring a change in the force, and wherein detecting the tenting comprises determining that the change in the force is greater than a preset force change range.

4. A method for detecting the tenting of tissue in a patient caused by a force-sensing medical probe, capable of use with a three-dimensional mapping and navigation system, inserted into the patient and contacting the tissue of the patient, comprising:
   measuring a force exerted by the medical probe on the tissue of a patient using the mapping and navigation system;
   measuring a spatial displacement of the probe using the mapping and navigation system while measuring the force; and
   detecting a tenting of the tissue responsively to a relation between the measured force and the measured displacement, wherein detecting the tenting comprises determining that the displacement is greater than a preset displacement range.

5. A method for detecting the tenting of tissue in a patient caused by a force-sensing medical probe, capable of use with a three-dimensional mapping and navigation system, inserted into the patient and contacting the tissue of the patient, comprising:
   measuring a force exerted by the medical probe on the tissue of a patient using the mapping and navigation system;
   measuring a spatial displacement of the probe using the mapping and navigation system while measuring the force;
   detecting a tenting of the tissue responsively to a relation between the measured force and the measured displacement; and measuring a size of the tenting in response to the measured displacement.

6. The method according to claim 3, 4, or 5 further comprising issuing a warning to an operator of the probe in response to detecting the tenting.

7. A method for detecting the tenting of tissue in a patient caused by a force-sensing medical probe, capable of use with a three-dimensional mapping and navigation system, inserted into the patient and contacting the tissue of the patient, comprising:
   measuring a force exerted by the medical probe on the tissue of a patient using the mapping and navigation system;
   measuring a spatial displacement of the probe using the mapping and navigation system while measuring the force;
   detecting a tenting of the tissue responsively to a relation between the measured force and the measured displacement; further comprising adjusting a map of coordinates of the tissue in response to detecting the tenting.

8. The method according to claim 6 further comprising issuing a warning to an operator of the probe in response to detecting tenting.

9. The method according to claim 7, wherein the tenting of the tissue comprises a conical formation in the tissue, and wherein adjusting the map comprises preparing the map absent a location of an apex of the conical formation.

10. The method according to claim 7, wherein preparing the map comprises determining a location of a base of the conical formation and using coordinates of the location of the base in preparing the map.

11. The method according to claim 1, 3, 4, 5, or 7 further comprising correcting the measured force in response to at least one of a heartbeat and a respiration of the patient.

12. An appartus, comprising:
   a force-sensing medical probe for insertion into a patient comprising:
      a force sensor configured to measure a force exerted by the probe on tissue of a patient; and
      a position transducer configured to measure a displacement of the probe while the force sensor is measuring the force; and
   a processor which is configured to detect a tenting of the tissue responsively to a relation between the measured force and the measured displacement, wherein detecting the tenting comprises confirming that the relation comprises a mathematically direct relationship between a first magnitude of a change in the measured force and a second magnitude of the measured displacement.

13. The apparatus according to claim 12, wherein the processor is configured to measure the change in the measured force in a direction defined by the measured displacement.

14. An apparatus comprising:
   a force-sensing medical probe for insertion into a patient comprising:

a force sensor configured to measure a force exerted by the probe on tissue of a patient; and a position transducer configured to measure a displacement of the probe while the force sensor is measuring the force; and a processor which is configured to detect a tenting of the tissue responsively to a relation between the measured force and the measured displacement wherein measuring the force comprises measuring a change in the force, and wherein detecting the tenting comprises determining that the change in the force is greater than a preset force change range.

15. An apparatus comprising:

a force-sensing medical probe for insertion into a patient comprising:

a force sensor configured to measure a force exerted by the probe on tissue of a patient; and a position transducer configured to measure a displacement of the probe while the force sensor is measuring the force; and a processor which is configured to detect a tenting of the tissue responsively to a relation between the measured force and the measured displacement, wherein detecting the tenting comprises determining that the displacement is greater than a preset displacement range.

16. An apparatus comprising:

a force-sensing medical probe for insertion into a patient comprising:

a force sensor configured to measure a force exerted by the probe on tissue of a patient; and a position transducer configured to measure a displacement of the probe while the force sensor is measuring the force; and a processor which is configured to detect a tenting of the tissue responsively to a relation between the measured force and the measured displacement, wherein the processor is configured to measure a size of the tenting in response to the measured displacement.

17. An apparatus comprising:

a force-sensing medical probe for insertion into a patient comprising:

a force sensor configured to measure a force exerted by the probe on tissue of a patient; and a position transducer configured to measure a displacement of the probe while the force sensor is measuring the force; and a processor which is configured to detect a tenting of the tissue responsively to a relation between the measured force and the measured displacement, wherein the processor is configured to adjust a map of coordinates of the tissue in response to detecting the tenting.

18. The apparatus according to claim 17, wherein the tenting of the tissue comprises a conical formation in the tissue, and wherein adjusting the map comprises preparing the map absent a location of an apex of the conical formation.

19. The apparatus according to claim 17, wherein preparing the map comprises determining a location of a base of the conical formation and using coordinates of the location of the base in preparing the map.

20. The apparatus according to claim 12, 13, 14, 15, 16, or 17, wherein the processor is configured to correct the measured force in response to at least one of a heartbeat and a respiration of the patient.

* * * * *